US012571804B2

(12) United States Patent
Luo et al.

(10) Patent No.: US 12,571,804 B2
(45) Date of Patent: Mar. 10, 2026

(54) AUTOMATIC TEST CARD FOR MULTI-BLOOD GROUP SYSTEM AND TEST METHOD

(71) Applicant: Chongqing University, Chongqing (CN)

(72) Inventors: Yang Luo, Chongqing (CN); Hong Zhang, Chongqing (CN)

(73) Assignee: Chongqing University, Chongqing (CN)

( * ) Notice: Subject to any disclaimer, the term of this patent is extended or adjusted under 35 U.S.C. 154(b) by 797 days.

(21) Appl. No.: 17/904,601

(22) PCT Filed: Mar. 3, 2021

(86) PCT No.: PCT/CN2021/078825
§ 371 (c)(1),
(2) Date: Aug. 19, 2022

(87) PCT Pub. No.: WO2021/175239
PCT Pub. Date: Sep. 10, 2021

(65) Prior Publication Data
US 2023/0097619 A1 Mar. 30, 2023

(30) Foreign Application Priority Data
Mar. 4, 2020 (CN) .......................... 202010143305.3

(51) Int. Cl.
*G01N 33/80* (2006.01)
*G01N 33/531* (2006.01)
*G01N 33/558* (2006.01)

(52) U.S. Cl.
CPC ........... *G01N 33/80* (2013.01); *G01N 33/531* (2013.01); *G01N 33/558* (2013.01)

(58) Field of Classification Search
None
See application file for complete search history.

(56) References Cited

U.S. PATENT DOCUMENTS 5,169,601 A 12/1992 Ohta et al.
2008/0199851 A1* 8/2008 Egan ................ G01N 33/54388
435/5

(Continued)

FOREIGN PATENT DOCUMENTS

CN 1924583 A 3/2007
CN 101603967 B 2/2015

(Continued)

OTHER PUBLICATIONS

Vella et al., "Measuring Markers of Liver Function Using a Micropatterned Paper Device Designed for Blood from a Fingerstick", Analytical Chemistry, 84, pp. 2883-2891, available online Feb. 12, 2012. (Year: 2012).*

(Continued)

*Primary Examiner* — Rebecca M Giere
(74) *Attorney, Agent, or Firm* — Fox Rothschild LLP

(57) ABSTRACT

The present disclosure provides an automatic test card for a multi-blood group system and a test method. The test card of a multi-blood group system includes four parts from top to bottom: a sample loading layer, a reaction layer, a color developing layer, and an identification layer. The automatic test card for a multi-blood group system and the test method combines blood group detection with encoding, and can rapidly and automatically identify and test multiple blood groups, reduce manual judgment errors, and improve detection efficiency. The method does not require special equipment and achieves rapid, accurate, automated, and portable detection of the blood groups.

17 Claims, 2 Drawing Sheets

(56) References Cited

U.S. PATENT DOCUMENTS

| | | | |
|---|---|---|---|
| 2009/0298191 A1 | 12/2009 | Whitesides et al. | |
| 2019/0086400 A1* | 3/2019 | Ehrenkranz | G01N 33/54366 |

FOREIGN PATENT DOCUMENTS

| | | |
|---|---|---|
| CN | 104361353 A | 2/2015 |
| CN | 104730258 A | 6/2015 |
| CN | 105441588 A | 3/2016 |
| CN | 103389384 B | 4/2016 |
| CN | 106124748 A | 11/2016 |
| CN | 106991679 A | 7/2017 |
| CN | 109324607 A | 2/2019 |
| CN | 107167616 B | 6/2019 |
| CN | 110060766 A | 7/2019 |
| CN | 110457972 A | 11/2019 |
| CN | 111443211 A | 7/2020 |
| GB | 2250342 A | 6/1992 |
| JP | 2009030997 A | 2/2009 |
| WO | 1997032213 A1 | 9/1997 |
| WO | 2012010666 A1 | 1/2012 |

OTHER PUBLICATIONS

Lopez-Ruiz et al., "Smartphone-Based Simultaneous pH and Nitrite Colorimetric Determination for Paper Microfluidic Devices", Analytical Chemistry, 86, pp. 9554-9562, available online Aug. 26, 2014. (Year: 2014).*

Noiphung et al., "A Novel paper-based assay for the simultaneous determination of RH typing and forward and reverse ABO blood groups", Biosensors and Bioelectronics 67, pp. 485-489, available online Sep. 8, 2014. (Year: 2014).*

Zhang, H. et al., "A dye-assisted paper-based point-of-care assay for fast and reliable blood grouping," Sci. Transl. Med. (2017); 9: eaaf9209 (11 pages).

Zhang, H. "Development and validation of fast and automatic blood grouping system," Chinese Master's Theses Full-Text Database, Medical and Health Sciences (2019); 2018(12): 81 pages.

* cited by examiner

AUTOMATIC TEST CARD FOR MULTI-BLOOD GROUP SYSTEM AND TEST METHOD

CROSS-REFERENCE TO RELATED APPLICATIONS

This patent application is the U.S. national phase of International Patent Application No. PCT/CN2021/078825, Automatic Test Card for Multi-Blood Group System and Test Method and filed on Mar. 3, 2021, which claims the benefit and priority of Chinese Patent Application No. 202010143305.3, entitled Automatic Test Card for Multi-Blood Group System and Test Method and filed on Mar. 4, 2020, the disclosures of which are incorporated by reference herein in their entirety as part of the present application.

TECHNICAL FIELD

The present disclosure belongs to the technical field of clinical examination and in vitro diagnosis and relates to an automatic test card for a multi-blood group system and to a test method.

BACKGROUND

Blood group refers to a type of surface antigens on blood components and generally refers to the typing of specific antigens on a red blood cell (RBC) membrane. More than 35 blood group systems have been discovered and recognized by the International Society of Blood Transfusion (ISBT). Among them, the ABO blood group system and the Rh blood group system are most closely related to human blood transfusion. In addition, MNS, Kell, and other systems are also closely associated with certain diseases. Blood grouping refers to the identification of cell surface antigens in blood components and is principally used in clinical blood transfusion, organ transplantation, and the treatment of neonatal hemolysis. Accurate blood grouping is very important. Due to blood group mismatch or heterotypic blood transfusion in emergency treatment, it is extremely apt to cause blood transfusion hemolysis, resulting in hemolytic anemia, renal failure, shock, and even death.

At present, blood grouping is commonly conducted by serum methods in clinical use, including conventional glass slide method, paper slip method, test tube method, and subsequently-developed cassette microcolumn gel method. In the serum method, blood grouping is achieved by judging the agglutination of the RBCs. In the serum method, RBC surface antigens in the blood and specific antibodies in the plasma of a subject are detected. If there is a corresponding antigen on the surface of the RBC, then the antigen may agglutinate with a corresponding antibody reagent. Likewise, if there is a specific antibody in the plasma of the subject, the antibody may agglutinate with the reagent RBC. Currently, the test tube method and the cassette microcolumn gel method are the most widely-used methods in clinical practice, which provide accurate results, desirable detection sensitivity, and high specificity. However, these two methods are time-consuming, and a large number of samples further increases the burden of clinical work and increases the risk of error occurrence, bringing great challenges to the clinical use of blood in emergency conditions. Moreover, most of the existing blood groups need to be tested by dedicated laboratory instruments, and the commonly-used blood grouping reagents need to be stored at 4° C. and are difficult to be long-term stored at room temperature, thereby bringing great inconvenience to outdoor blood grouping. Furthermore, due to limitations of reagents and testing conditions, the cost of instruments and reagents is rather high, bringing difficulties to blood grouping in economically backward areas. This hinders the improvement of the overall medical level in grassroots communities and increases the economic burden on patients.

With the development of biotechnology, portable blood group test cards have been developed rapidly. Chinese patent CN101603967B discloses a method and a kit for rapid detection of human ABO/Rh/MN blood groups. By pre-coating, the antibody anti-A or anti-B or anti-D or anti-M or anti-N blood group is immobilized on a test strip. After washing the test strip with a washing solution, the blood group of a blood sample to be tested is determined by observing the sample pad for the presence of residual agglutinated RBCs. The test card is portable and has a high detection speed, but it can only detect ABO positive type. If there is a discrepancy between the positive and negative ABO types, test errors are prone to occur. Chinese patent CN103389384B discloses an immunofluorescence chromatography test strip for detection of Miltenberger blood group antibody and a detection method thereof, and the detection method can quantitatively measure Miltenberger blood group by fluorescence. However, fluorescence detection is restricted in practical application and promotion due to the need for large-scale professional instruments and is not applicable in areas with scarce resources and underdeveloped areas. Chinese patent CN107167616B provides a method and a device for blood grouping, in which method, blood to be tested was subjected to immunoreaction with the antibodies to collect color images after multiple reaction chambers were coated with different antibodies, and the color images were converted into grayscale images, and blood grouping results were determined according to grayscale values. Although this method provides certain support for automated detection, two different colors may have close grayscale values, and this would cause errors in the detection results and increase the false-negative rate and false positive rate during the detection. Moreover, it is impossible to identify whether it is a blood sample.

Most of the above methods can detect a single blood group or certain antigens in the blood group system, and do not allow automatic and synchronous detection of common blood groups (including Rh blood group and MNS blood group). Conventional technologies are time-consuming, require additional special equipment, and have no universal detection method, and automatic detection is not fully realized. It is difficult to meet the requirement of use in emergency and economically-backward areas, thereby greatly limiting practical values in use. Therefore, a rapid, accurate, portable, and universal automatic blood grouping technology and method need to be developed to rescue critical patients, respond to emergencies, and help improve medical and health care in resource-scarce areas.

SUMMARY

Given this, the objective of the present disclosure is to provide an automatic test card for the multi-blood group system and provide a test method. The present disclosure combines blood grouping with barcode and two-dimensional code technologies, without the need for large special equipment. The multi-blood group system and the test method can identify and test the multiple blood groups rapidly and automatically, reduce manual judgment errors, and improve detection efficiency. The method can achieve rapid, accurate, automated, and portable detection of the blood groups.

To achieve the above objective, the present disclosure provides the following technical solutions.

The present disclosure provides an automatic test card of a multi-blood group system, including four layers from top to bottom: a sample loading layer, a reaction layer, a color developing layer, and an identification layer; wherein the sample loading layer is provided with a sample loading hole, the reaction layer is provided with a whole blood pad or a filter pad for filtering RBCs from whole blood, and bottom of the sample loading hole is connected to the whole blood pad or the filter pad; an end of the whole blood pad is connected to a plurality of antibody pads pre-coated with blood group antibodies, and an end of the filter pad is connected to antigen pads pre-coated with blood group antigens via a delay pad; the reaction layer is independently provided with a quality control strip; the color developing layer is provided with a plurality of color developing areas connected to an end of the antibody pad or the antigen pad; the identification layer is reversely connected to the color developing layer and comprises a two-dimensional code positioning area, a calibration area, a plurality of test areas, and a subject information area; and positions of the test areas and positions of the color developing areas are aligned with each other one by one.

Preferably, the test card has a three-dimensional or two-dimensional structure and is obtained by a method selected from test paper serial connection, origami technology, wax printing, photosensitive seal, photoetching, or three-dimensional (3D) printing.

Preferably, the sample loading layer and the reaction layer are arranged separately or integrated into one piece.

Preferably, the sample loading layer is made of glass fiber, cotton pulp paper, napkin, filter paper, gauze, or hydrogel; the sample loading hole is round or square, and the sample loading layer is treated using a technology selected from wax printing and photolithography to form a hydrophilic area and a hydrophobic area.

Preferably, the whole blood pad, the antibody pad, the delay pad, and the antigen pad each are made of a material selected from non-woven fabrics, non-woven paper, filter paper, cotton pulp paper, and glass fiber with a pore size of 8 μm to 20 μm.

Preferably, the filter pad is made of Prussian blue membrane, glass fiber, graphene cloth, carbon cloth, carbon paper, whole blood separation membrane, or nitrocellulose membrane.

Preferably, the antibody pad is pre-coated with commercialized ABO, Rh, MNS, Kell, P, Kidd, Duffy blood group antibodies, and IgM, IgG, and IgM-IgG mixed antibodies may be used. And the antibodies can be immobilized by methods such as freeze-drying at –80° C., plasma treatment, covalent bond coupling, vacuum drying at 20° C. to 50° C., immunomagnetic bead binding, or electrostatic adsorption.

Preferably, the quality control strip includes a quality control area corresponding to the position of the antibody pad; the quality control area is coated with PBS or a normal saline reagent, and dried at 30° C. to 50° C.; the rest sequences and the coating reagent are consistent with that for other strips.

Preferably, the delay pad is used for regulating the reaction time of antibody detection and the delay is achieved using a chemical method or a physical method. In the chemical method, saccharides (including sucrose, dextran, and pectin), paraffin, or alkyl ketene dimers are pre-coated on the delay pad. In the physical method, the shape of the delay pad is changed or the length and width of the delay pad are increased. The delay pad may be pre-coated and immobilized by freeze-drying at –80° C. or vacuum dried at 30° C. to 50° C.

Preferably, the antigen pad is pre-coated with ABO blood group antigens, including A1, A2, B, and O RBCs, and the ABO blood group antigens are immobilized by freeze-drying at –80° C., vacuum drying at 4° C. to 30° C., immunomagnetic bead binding, or electrostatic adsorption; alternatively, fresh RBCs are used as antigen and added directly on the antigen pad. The A1, A2, B, and O RBCs are commercial reagents.

Preferably, the color-developing layer is made of nitrocellulose membrane, cellulose acetate membrane, or polyester cellulose membrane. The color development method involves color change or gray value change; the color developing area may be any shape of square, rectangle, or circle; the pre-coating reagent may be nanoparticles or a dye; the nanoparticles are selected from latex particles, gold nanoparticles, and silver nanoparticles; and the dye is selected from a biuret reagent, methyl green, pyronin, a bromothymol blue solution, and ninhydrin.

The color developing area may be any shape of square, rectangle, triangle, rhombus, or circle.

Preferably, the identification layer is made of printing paper, cotton paper, or blotting paper, and the positioning area, the calibration area, and the subject information area is visualized by wax printing, laser printing, or photosensitive seal; the positioning area is used for automatic positioning and deviation correction in automatic detection, and may be any shape of circle-in-square, square-in-circle, concentric circles, and square-in-square; the calibration area is used for color calibration to prevent interference from an external environment and a photographing instrument The calibration area includes 5 to 18 color blocks with colors represented by RGB including any combination between (0, 0, 0) to (255, 255, 255) The subject information area may include a two-dimensional code, a three-dimensional code, or a barcode used for registration and storage of subject information, and the two-dimensional code and the three-dimensional code is selected from Data Matrix, MaxiCode, Aztec, or QR Code, and the barcode is selected from EAN, UPC or Codabar. The information includes basic name, age, gender, ID number, department, specimen type, inspection item, inspector, and remarks.

Preferably, the test area overlaps with the color developing area and has a hollow structure or a transparent membrane. The hollow structure is formed by laser cutting, chemical etching, or manual cutting, and the transparent membrane is made of polyvinyl chloride, polyethylene, polypropylene, polystyrene, or resin.

The present disclosure further provides an automatic test method for a multi-blood group system using the test card, including the following steps: adding whole blood to the sample loading hole, adding PBS, normal saline, or ultrapure water after the whole blood to blood separation and an antigen-antibody reaction are carried out for 30 sec to 1 min, observing a color change in the test area with naked eyes after 10 sec, and interpreting results by recognition with the naked eyes or with automatic code identification software.

Preferably, fresh or anticoagulant-treated whole blood is injected into the sample loading hole.

Preferably, reverse typing of the ABO blood group requires a sample volume of 50 μL to 250 μL, and another detection of a single target requires a sample volume of 5 μL to 15 μL.

Preferably, the automatic identification software is generally installed in a common electronic device such as a smartphone, a computer, and a hand-held scanner.

Preferably, the identification process of the automatic identification software includes: performing image acquisition, image positioning and segmentation, identifying the samples, identifying the two-dimensional code or the barcode, and conducting contrastive analysis by comparison with a built-in database to acquire information in an image and displaying a blood group result automatically.

More preferably, the image acquisition is realized by photographing, scanning, or video recording.

More preferably, the image positioning and segmentation are carried out by the following steps: distinguishing an inner or outer boundary of the positioning area using a FindContours function of OpenCV. And the function includes five parameters, the first parameter is a result obtained from binarization processing on a collected pattern, the second parameter is a memory device in which the contours that FindContours finds are stored, the third parameter is level, the fourth parameter is type in which a tree structure is adopted, and the fifth parameter is node fitting mode in which complete search is conducted. The contours are retrieved from a binary image and used as a contour tree, and a pointer Firstcontour is filled by the function to generate a hierarchical structure value. A threshold value can be dynamically found by a Shimadzu method, and all points are converted from a freeman code form to a point-sequence form; the contour of the pattern of the positioning point pattern in the positioning area is identified, image position and shape differences caused by different shooting angles are rectified, and the geometric deformation identified at the position is mapped to the position identified in the test area.

More preferably, a specific method of the identification of the samples includes the steps: extracting a color in the test area, determining the depth of a test object using a color strip pattern, finding a similarity based on the color RGB contrast of calibration area strip, and determining the real output result based on the corresponding position of each test area on the calibration area stripe; comparing the detection value obtained in the test area with a color stripe in the calibration area from left to right in sequence to obtain an actual value without being affected by color difference, light, and angle of the photographing. More preferably, the identification by the two-dimensional code or the barcode is achieved by a Zbar toolkit or a ZXing toolkit.

The interpretation criteria are as follows: based on the coating reaction time, the occurrence of red, brown, or suntan color indicates that the corresponding test area is negative, and the occurrence of white, blue, or yellow color indicates that the corresponding test area is positive.

Preferably, based on the automatic comparison between the actual value and the built-in database, a result of blood group interpretation is output on a software interface automatically.

The present disclosure has the following beneficial effects.

In the present disclosure, the blood group test card is combined with the encoding technology, and rapid and portable blood grouping of trace samples is achieved by multi-layer blood group test cards. The card is disposable, safe, and convenient to prevent cross-contamination. Automated result interpretation solves the problem of large samples in clinical testing. The use of the encoding technology allows for automatic positioning, deviation correction, and calibration, solving the low test stability caused by deviation of photographing color, angle, and mobile phone model, thereby improving test stability and accuracy. Patient information is automatically associated with test results without manual input, reducing operator workload. The automatic identification software does not require professional equipment and can be installed on general-purpose smartphones, computers, and other equipment, greatly reducing the burden of grass-root health care work. In summary, the test card and the test method can rapidly and automatically identify and test multiple blood groups using trace amounts of blood, reduce manual judgment errors, and improve detection efficiency. The method allows for rapid, accurate, automated, and portable detection of the blood groups.

BRIEF DESCRIPTION OF THE DRAWINGS

To make the objectives, technical solutions, and beneficial effects of the present disclosure clearer, the present disclosure provides the following drawings.

FIG. 1a shows a sample loading layer, FIG. 1B shows a reaction layer, FIG. 1c shows a color developing layer and FIG. 1d shows an identification layer.

Figure 1A:
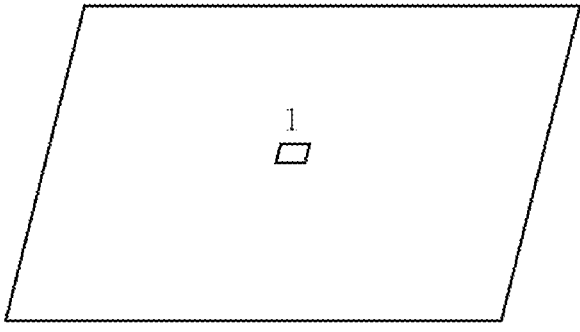
FIG. 1a to FIG. 1d show the structural schematic diagrams of the test card of the present disclosure, where

Reference numerals: 1—sample loading hole; 2—filter pad; 3—whole blood pad; 4—antibody pads; 5—delay pad; 6—antigen pad; 7—color developing area; 8—test area; 9—positioning area; 10—calibration area; and 11—subject information area.

DETAILED DESCRIPTION OF THE EMBODIMENTS

The examples of the present disclosure are described in detail below by referring to the drawings.

Example 1

Automatic Detection of Human ABO Blood Group and Rh(C/c/D/E/e) Blood Group

Figure 1B:
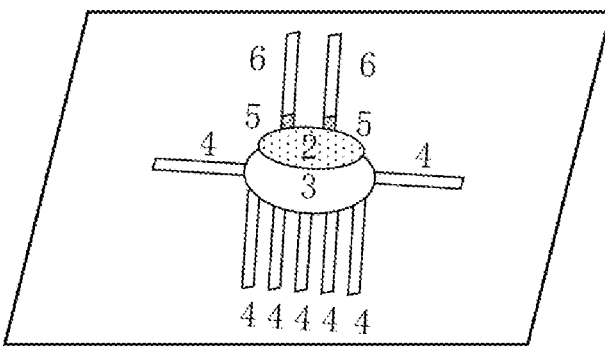
Figure 1C:
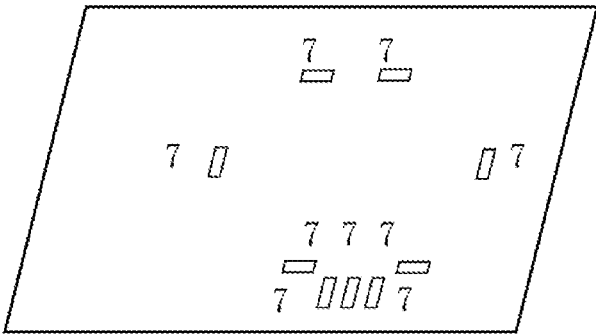
Figure 1D:
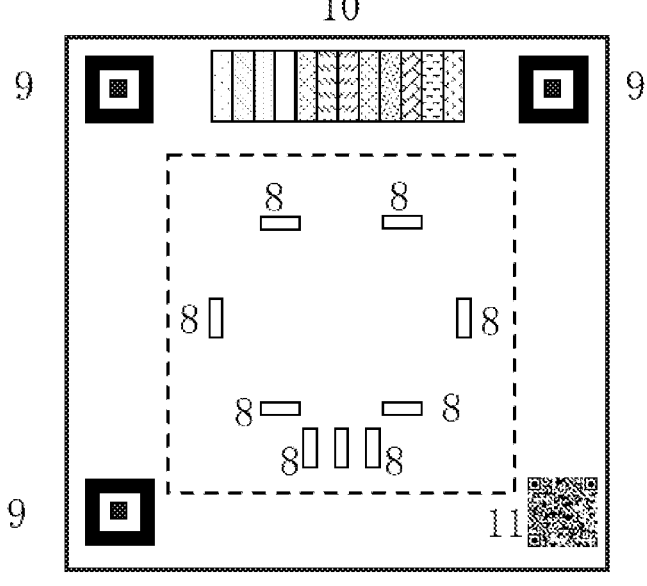

A three-dimensional test card structure was constructed using wax printing technology, as shown in FIG. 1a to FIG. 1d. The sample loading layer and the reaction layer were set separately, and the sample loading hole 1 was circular. The sample loading layer was made of glass fiber, the whole blood pad 3, the antibody pad 4, the delay pad 5, and the antigen pad 6 of the reaction layer each were made of non-woven paper, and the whole blood separation membrane was used as the material of the filter pad 2.

The antibody pad 4 was pre-coated with 7 antibodies anti-A, anti-B, anti-C, anti-c, anti-D, anti-E, and anti-e, which were of IgM type. The quality control area was infiltrated with normal saline and dried, the delay pad 5 was pre-coated with dextran, and immobilized after freeze-drying at −80° C., the color developing layer was made of nitrocellulose membrane, and the color developing areas included 8 square areas, which corresponded to 7 test results (numbered 1 to 7) of ABO and Rh blood groups as well as the No. 8 quality control area, and were pre-coated with methyl green. The color developing area 7 was a square in shape, the identification layer was made of printing paper, and the positioning area 9, the calibration area 10, and the subject information area 11 were visualized by wax printing. The positioning area 9 had a circle-in-square pattern, and the calibration area 10 was composed of 6 color blocks, with RGB being (68, 114, 196), (240, 142, 24), (44, 220, 65), (218, 46, 148), (220, 78, 44), and (41, 219, 223). The subject information area 11 included a QR two-dimensional code, and the information contained name, age, gender, ID number, department, specimen type, inspection item, inspector, and remarks. The sample loading layer, the reaction layer, the color developing layer, and the identification layer were assembled from top to bottom. Test area 8 overlapped with the color developing area, and a laser-cut hollow structure was adopted.

Specific Production Process:

Seventy microliters of whole blood was added to the sample loading hole 1, and 140 µL of ultrapure water was added after 30 seconds, number 1 to number 8 color developing areas were observed for color changes, and a picture was taken with a mobile phone against the test card. Ten seconds later, a blood group result automatically popped up on an interface of the mobile phone. Green meant positive and yellow meant negative.

A, B, C, c, D, E, and e corresponded to the color developing areas No. 1 to No. 7, and test area 8 was the quality control result.

Results are shown in Table 1.

TABLE 1

| Test results of Example 1 | | |
| --- | --- | --- |
| Color development (color developing areas No. 1-8) | Results | Blood group |
| 1, 3, 5, and 6 were green, the rest were yellow | A positive and CDE positive | Types A and Rh (CDE) |
| 1, 2, 3, 5, and 6 were green, the rest were yellow | A and B positive and CDE positive | Types AB and Rh (CDE) |
| 3, 4, 5, and 6 were green, the rest were yellow | A and B negative and CcDE positive | Types O and Rh (CcDE) |
| 2, 3, 4, 5, 6, and 7 were green, the rest were yellow | B positive and CcDEe positive | Types B and Rh (CcDEe) |

Not all results are listed in the above table, other results were deduced analogously by referring to the above data, and the results were determined according to a same criterion.

Example 2

Automatic Detection of Human MNS, Kell, P, Kidd Blood Groups

A three-dimensional test card structure was constructed using origami technology, as shown in FIG. 1a to FIG. 1d. The sample loading layer and the reaction layer were integrated into one piece, and the sample loading hole 1 was square in shape, the whole blood pad 3, the antibody pad 4, the delay pad 5 and the antigen pads 6 of the reaction layer were made of an exemplary material of filter paper, and a filter pad 2 was made of an exemplary material of carbon paper.

The antibody pad was pre-coated with 9 antibodies anti-M, anti-N, anti-S, anti-s, anti-K, anti-k, anti-P, anti-Jka, and anti-Jkb, which were of IgM-IgG mixed types and immobilized after vacuum drying at 30° C. The quality control area was infiltrated with ultrapure water and dried, the color developing layer was made of cellulose acetate membrane, and the color developing areas had 10 square areas, which corresponded to 9 test results (numbered 1 to 9) of MNS, Kell, P and Kidd blood groups and the No. 10 quality control area, and were pre-coated with ninhydrin. The color developing area 7 was a square in shape, the identification layer was made of printing paper, and the positioning area 9, the calibration area 10, and the subject information area 11 were visualized by wax printing. The positioning area 9 had a circle-in-square pattern, and the calibration area 10 was composed of 10 color blocks, with RGB being (34, 151, 230), (229, 100, 35), (208, 226, 38), (224, 40, 202), (236, 28, 127), (41, 219, 223), (65, 215, 49), (204, 84, 60), (58, 174, 206), and (48, 6, 22). The subject information area 11 included a QR two-dimensional code, and the information contained name, age, gender, ID number, department, specimen type, inspection item, inspector, and remarks. The sample loading layer, the reaction layer, the color developing layer, and the identification layer were assembled from top to bottom. Test area 8 overlapped with the color developing area, and a laser-cut hollow structure was adopted.

Specific Production Process:

One hundred microliters of whole blood was added to the sample loading hole 1, and 200 µL of ultrapure water was added after 1 minute, number 1 to number 8 color developing areas were observed for color changes, and a picture was taken with a mobile phone against the test card. Ten seconds later, a blood group result automatically popped up on an interface of the mobile phone; blue meant positive, and red meant negative.

M, N, S, s, K, k, P, Jka, Jkb corresponded to the color developing areas No. 1 to No. 9, and test area 10 was the quality control result.

Results are shown in Table 2.

TABLE 2

| Test results of Example 2 | | |
| --- | --- | --- |
| Color development (color developing areas No. 1-10) | Results | Blood group |
| 1, 2, 3, 5, 6, 7, and 8 were blue, the rest were red | M, N, S, K, k, P, Jka positive | Types MNS (MNS), Kell (K + k+), P and Kidd (Jka + b−) |
| 1, 2, 3, 4, 5, 6, and 7 were blue, the rest were red | M, N, S, s, K, k, P positive | Types MNS (MNS), Kell (K + k+), P and Kidd (Jka − b−) |
| 1, 2, 5, and 7 were blue, the rest were red | M, N, K, P positive | Types MNS (MN), Kell (K + k−), P and Kidd (Jka − b−) |
| 2, 3, 4, 5, 7, and 9 were blue, the rest were red | N, S, s, K, k, P, Jkb positive | Types MNS (NSs), Kell (K + k−), P and Kidd (Jka − b+) |

Not all results are listed in the above table, other results were deduced analogously by referring to the above data, and the results were determined according to a same criterion.

Example 3

Automatic Detection of Human ABO Positive and Negative Typing and Rh(C/c/D/E/e) Blood Groups A three-dimensional test card structure was constructed using wax printing technology, as shown in FIG. 1a to FIG. 1d. The sample loading layer and the reaction layer were set separately, and the sample loading hole 1 was circular in shape; the sample loading layer was made of filter paper; the whole blood pad 3, the antibody pad 4, the delay pad 5 and the antigen pads 6 of the reaction layer each were made of non-woven fabrics and the filter pad 2 was made of glass fiber.

The antibody pad was pre-coated with 7 antibodies anti-A, anti-B, anti-C, anti-c, anti-D, anti-E, and anti-e, which were of IgM type. The quality control area was infiltrated with normal saline and dried, the delay pad 5 was pre-coated with pectin, and immobilized after freeze-drying at −80° C., ABO blood groups A1, A2, B, and O RBCs were added to the antigen pad to detect ABO blood group reverse typing, the color developing layer was made of nitrocellulose membrane, and the color developing areas included 8 square areas, which corresponded to 7 test results (numbered 1 to 7) of ABO and Rh blood groups and the No. 8 quality control area and were pre-coated with methyl green. The color developing area 7 was a square in shape, the identification layer was made of printing paper, and the positioning area 9, the calibration area 10, and the subject information area 11 were visualized by wax printing. The positioning area 9 had a circle-in-square pattern, and the calibration area 10 was composed of 15 color blocks, with RGB being (68, 114, 196), (240, 142, 24), (44, 220, 65), (218, 46, 148), (220, 78, 44), (41, 219, 223), (50, 148, 46), (80, 44, 78), (150, 150, 225), (60, 15, 210), (120, 90, 50), (41, 165, 223), (140, 20, 220), (150, 45, 80), and (41, 165, 223). The subject information area 11 included a barcode, and the information contained name, age, gender, ID number, department, specimen type, inspection item, inspector, and remarks. The sample loading layer, the reaction layer, the color developing layer, and the identification layer were assembled from top to bottom. Test area 8 overlapped with the color developing area, and a polyethylene transparent membrane structure was adopted.

Specific Production Process:

Three hundred microliters of whole blood was added to the sample loading hole 1, and 180 μL of ultrapure water was added after 60 seconds, number 1 to number 8 color developing areas were observed for color changes, and a picture was taken with a mobile phone against the test card. Ten seconds later, a blood group result automatically popped up on an interface of the mobile phone. Green meant positive and yellow meant negative.

Blood groups A, B, C, c, D, E, and e corresponded to the color developing areas No. 1 to No. 7, A1, A2, B, and O RBCs corresponded to the color developing areas 8 to 11, and the test area 12 was the quality control result.

Results are shown in Table 3.

TABLE 3

| Test results of Example 3 | | |
|---|---|---|
| Color development (color developing areas No. 1-12) | Results | Blood group |
| 1, 3, 5, 6, and 10 were green, the rest were yellow | A positive and CDE positive | Types A and Rh (CDE) |
| 1, 2, 3, 5, 6, and 11 were green, the rest were yellow | A and B positive and CDE positive | Types AB and Rh (CDE) |
| 3, 4, 5, 6, 8, and 10 were green, the rest were yellow | A and B negative and CcDE positive | Types O and Rh (CcDE) |
| 2, 3, 4, 5, 6, 7, and 9 were green, the rest were yellow | B positive and CcDEe positive | Types B and Rh (CcDEe) |

Not all results are listed in the above table, other results were deduced analogously by referring to the above data, and the results were determined according to a same criterion.

Finally, the above-preferred embodiments are only used to illustrate the technical solutions of the present disclosure but not to limit them. Although the present disclosure has been described in detail through the above-preferred embodiments, a person skilled in the art should understand that various changes can be made in form and detail without departing from the scope defined by the claims of the present disclosure.

What is claimed is:

1. A test card of a multi-blood group system, comprising four layers from top to bottom: a sample loading layer, a reaction layer, a color developing layer, and an identification layer;

the sample loading layer being provided with a sample loading hole, the reaction layer being provided with a whole blood pad or a filter pad for filtering red blood cells (RBCs) from whole blood, and bottom of the sample loading hole being connected to the whole blood pad or the filter pad; an end of the whole blood pad being connected to a plurality of antibody pads pre-coated with blood group antibodies, or an end of the filter pad being connected to antigen pads pre-coated with blood group antigens via a delay pad; the reaction layer being independently provided with a quality control strip;

wherein the color developing layer is provided with a plurality of color developing areas connected to an end of the antibody pad or the antigen pad; the identification layer is reversely connected to the color developing layer, and comprises three two-dimensional code positioning areas, a calibration area, a plurality of test areas, and a subject information area; and positions of the test areas and positions of the color developing areas being aligned with each other one-to-one such that the test areas overlaps with the color developing areas and provides a hollow hole or a transparent membrane on the test areas; and the identification layer has a shape of square, the three two-dimensional code positioning areas are distributed in three corners of the square, and the subject information area includes a QR two-dimensional code, a three-dimensional code, or a barcode used for registration and storage of subject information and is distributed in the fourth corner of the square; and the calibration area is composed of 6 color blocks, with RGB being (68, 114, 196), (240, 142, 24), (44, 220, 65), (218, 46, 148), (220, 78, 44), and (41, 219, 223).

2. The test card according to claim 1, wherein the test card has a three-dimensional or two-dimensional structure.

3. The test card according to claim 1, wherein the sample loading layer is made of glass fiber, cotton pulp paper, napkin, filter paper, gauze, or hydrogel, the sample loading hole is round or square, and the sample loading layer is treated using a technology selected from wax printing and photolithography to form a hydrophilic area and a hydrophobic area; the whole blood pad, the antibody pad, the delay pad, and the antigen pad each are made of a material selected from non-woven fabrics, non-woven paper, filter paper, cotton pulp paper, and glass fiber with a pore size of 8 μm to 20 μm; and the filter pad is made of Prussian blue membrane, glass fiber, graphene cloth, carbon cloth, carbon paper, whole blood separation membrane, or nitrocellulose membrane.

4. The test card according to claim 1, wherein the antibody pad is pre-coated with commercialized ABO, Rh, MNS, Kell, P, Kidd, Duffy blood group antibodies which are immobilized by freeze-drying at 80° C., plasma treatment, covalent bond coupling, vacuum drying at 20° C. to 50° C., immunomagnetic bead binding, or electrostatic adsorption; and the antigen pad is pre-coated with ABO blood group antigens selected from A1, A2, B, and O RBCs; and the ABO blood group antigens are immobilized by freeze-drying at 80° C., vacuum drying at 4° C. to 30° C., immunomagnetic bead binding, or electrostatic adsorption; or alternatively, fresh RBCs are used as the antigen and added directly on the antigen pad.

5. The test card according to claim 1, wherein the delay pad achieves delay chemically by pre-coating with saccharides, paraffin, or alkyl ketene dimers, or physically by changing the shape of the delay pad or increasing the length and width of the delay pad.

6. The test card according to claim 1, wherein the color developing layer is made of nitrocellulose membrane, cellulose acetate membrane, or polyester cellulose membrane; color developing is performed on the color developing layer by a method selected from color change and gray value change; each of the color developing areas is any shape of a square, a rectangle, or a circle; the pre-coated antibody pads or the pre-coated antigen pads are pre-coated with nanoparticles or a dye, and the nanoparticles are selected from latex particles, gold nanoparticles, and silver nanoparticles, and the dye is selected from a biuret reagent, methyl green, pyronin, a bromothymol blue solution, and ninhydrin.

7. The test card according to claim 1, wherein the identification layer is made of printing paper, cotton paper, or blotting paper, and the positioning area, the calibration area, and the subject information area are visualized by wax printing, laser printing, or photosensitive seal; the positioning area is used for automatic positioning and deviation correction in automatic detection; the calibration area is used for color calibration to prevent interference from external environment and a photographing instrument.

8. The test card according to claim 1, wherein the hollow structure is formed by laser cutting, chemical etching, or manual cutting, and the transparent membrane is made of polyvinyl chloride, polyethylene, polypropylene, polystyrene, or resin.

9. An automatic test method for a multi-blood group system using the test card according to claim 1, comprising the following steps: adding whole blood to the sample loading hole, after 30 sec to 1 min adding PBS, normal saline, or ultrapure water to the sample loading hole, observing a color change in the test area with naked eyes after 10 sec, and interpreting results with automatic identification software; wherein the automatic identification software is capable of being installed in a common electronic device comprising a smartphone, a computer, and a scanner;

wherein the test card comprises four layers from top to bottom: a sample loading layer, a reaction layer, a color developing layer, and an identification layer;

wherein the sample loading layer is provided with a sample loading hole, the reaction layer is provided with a whole blood pad or a filter pad for filtering red blood cells (RBCs) from whole blood, and bottom of the sample loading hole is connected to the whole blood pad or the filter pad; an end of the whole blood pad is connected to a plurality of antibody pads pre-coated with blood group antibodies, or an end of the filter pad is connected to antigen pads pre-coated with blood group antigens via a delay pad; the reaction layer is independently provided with a quality control strip;

wherein the color developing layer is provided with a plurality of color developing areas connected to an end of the antibody pad or the antigen pad; the identification layer is reversely connected to the color developing layer, and comprises three two-dimensional code positioning areas, a calibration area, a plurality of test areas, and a subject information area; and positions of the test areas and positions of the color developing areas being aligned with each other one-to-one such that the test areas overlaps with the color developing areas and provides a hollow hole or a transparent membrane on the test areas; and the identification layer has a shape of square, the three two-dimensional code positioning areas are distributed in three of corners of the square, and the subject information area includes a QR two-dimensional code, a three-dimensional code, or a barcode used for registration and storage of subject information and is distributed in the fourth corner of the square; and the calibration area is composed of 6 color blocks, with RGB being (68, 114, 196), (240, 142, 24), (44, 220, 65), (218, 46, 148), (220, 78, 44), and (41, 219, 223).

10. The test method according to claim 9, wherein an identification process of the automatic identification software comprises: performing image acquisition, image positioning and segmentation, identification and sampling, and identification of subject information by the two-dimensional code or the barcode; and conducting contrastive analysis with a built-in database, automatically acquiring information in an image, and displaying a blood group result.

11. The automatic test method for a multi-blood group system using the test card according to claim 9, wherein the test card has a three-dimensional or two-dimensional structure.

12. The automatic test method for a multi-blood group system using the test card according to claim 9, wherein the sample loading layer is made of glass fiber, cotton pulp paper, napkin, filter paper, gauze, or hydrogel, the sample loading hole is round or square, and the sample loading layer is treated using a technology selected from wax printing and photolithography to form a hydrophilic area and a hydrophobic are; the whole blood pad, the antibody pad, the delay pad, and the antigen pad each are made of a material selected from non-woven fabrics, non-woven paper, filter paper, cotton pulp paper, and glass fiber with a pore size of 8 μm to 20 μm; and the filter pad is made of Prussian blue membrane, glass fiber, graphene cloth, carbon cloth, carbon paper, whole blood separation membrane, or nitrocellulose membrane.

13. The automatic test method for a multi-blood group system using the test card according to claim 9, wherein the antibody pad is pre-coated with commercialized ABO, Rh, MNS, Kell, P, Kidd, Duffy blood group antibodies which are immobilized by freeze-drying at 80° C., plasma treatment, covalent bond coupling, vacuum drying at 20° C. to 50° C., immunomagnetic bead binding, or electrostatic adsorption; and the antigen pad is pre-coated with ABO blood group antigens selected from A1, A2, B, and O RBCs; and the ABO blood group antigens are immobilized by freeze-drying at 80° C., vacuum drying at 4° C. to 30° C., immunomagnetic bead binding, or electrostatic adsorption; or alternatively, fresh RBCs are used as the antigen and added directly on the antigen pad.

14. The automatic test method for a multi-blood group system using the test card according to claim 9, wherein the delay pad achieves delay chemically by pre-coating with saccharides, paraffin, or alkyl ketene dimers, or physically by changing the shape of the delay pad or increasing the length and width of the delay pad.

15. The automatic test method for a multi-blood group system using the test card according to claim 9, wherein the color developing layer is made of nitrocellulose membrane, cellulose acetate membrane, or polyester cellulose membrane; color developing is performed on the color developing layer by a method selected from color change and gray value change; each of the color developing areas is any shape of a square, a rectangle, or a circle; the pre-coated antibody pads or the pre-coated antigen pads are pre-coated with nanoparticles or a dye, and the nanoparticles are selected from latex particles, gold nanoparticles, and silver nanoparticles, and the dye is selected from a biuret reagent, methyl green, pyronin, a bromothymol blue solution, and ninhydrin.

16. The automatic test method for a multi-blood group system using the test card according to claim 9, wherein the identification layer is made of printing paper, cotton paper, or blotting paper, and the positioning area, the calibration area, and the subject information area are visualized by wax printing, laser printing, or photosensitive seal; the positioning area is used for automatic positioning and deviation correction in automatic detection; the calibration area is used for color calibration to prevent interference from external environment and a photographing instrument; and the subject information area includes a two-dimensional code, a three-dimensional code, or a barcode used for registration and storage of subject information.

17. The automatic test method for a multi-blood group system using the test card according to claim 9, wherein the hollow structure is formed by laser cutting, chemical etching, or manual cutting, and the transparent membrane is made of polyvinyl chloride, polyethylene, polypropylene, polystyrene, or resin.

\* \* \* \* \*